(12) United States Patent
Gesotti (10) Patent No.: US 7,369,896 B2
(45) Date of Patent: May 6, 2008

(54) SYSTEMS AND METHODS FOR TREATING MOVEMENT DISORDERS

(75) Inventor: Phillip E. Gesotti, Manassas, VA (US)

(73) Assignee: Lockheed Martin Corporation, Manassas, VA (US)

( * ) Notice: Subject to any disclaimer, the term of this patent is extended or adjusted under 35 U.S.C. 154(b) by 564 days.

(21) Appl. No.: 10/693,792

(22) Filed: Oct. 24, 2003

(65) Prior Publication Data

US 2004/0088025 A1    May 6, 2004

Related U.S. Application Data

(60) Provisional application No. 60/420,769, filed on Oct. 24, 2002.

(51) Int. Cl.
*A61N 1/36* (2006.01)

(52) U.S. Cl. .......................................... 607/49; 607/45

(58) Field of Classification Search .................. 607/48, 607/49; 434/255; 128/905; 340/573.1
See application file for complete search history.

(56) References Cited

U.S. PATENT DOCUMENTS

| 4,165,750 A | 8/1979 | Aleev et al. |
|---|---|---|
| 4,340,063 A | 7/1982 | Maurer |
| 4,558,704 A | 12/1985 | Petrofsky |
| 4,569,352 A | 2/1986 | Petrofsky et al. |
| 4,580,339 A | 4/1986 | Ioffe |
| 4,669,480 A | 6/1987 | Hoffman |
| 4,697,808 A | 10/1987 | Larson et al. |
| 4,754,759 A | 7/1988 | Allocca |
| 4,759,368 A | 7/1988 | Spanton et al. |
| 4,769,881 A | 9/1988 | Pedigo |
| 4,785,813 A | 11/1988 | Petrofsky |
| 4,917,092 A | 4/1990 | Todd et al. |

(Continued)

FOREIGN PATENT DOCUMENTS

EP    0506398    9/1992

(Continued)

OTHER PUBLICATIONS

Alon, "High Voltage Stimulation: Effects of electrode size on basic excitatory responses," *Phy. Ther.*, 1985, 890-895, vol. 65.

(Continued)

*Primary Examiner*—George R. Evanisko
*Assistant Examiner*—Michael Kahelin
(74) *Attorney, Agent, or Firm*—Fogg & Powers LLC (57) ABSTRACT

Movement timing stimulator systems and methods that aid in the relief of the symptoms of neurological movement disorders are provided. In one embodiment, a method of improving a patient's gait is provided. The method includes producing a plurality of stimulation prompts at a plurality of stimulation points using multiple stimulation channels. The plurality of stimulation points is located symmetrically on each leg. The method further includes applying the plurality of stimulation prompts in a timed periodic fashion across the plurality of stimulation points and activating a return electrode whenever one of the multiple stimulation channels on an associated leg is active. The plurality of stimulation prompts are not synchronized with the patient's gait. Each of the multiple stimulation channels is associated with a stimulation electrode at one of the plurality of stimulation points.

24 Claims, 7 Drawing Sheets

U.S. PATENT DOCUMENTS

| | | | |
|---|---|---|---|
| 4,922,908 | A | 5/1990 | Morawetz et al. |
| 4,989,605 | A | 2/1991 | Rossen |
| 5,038,797 | A | 8/1991 | Batters |
| 5,121,747 | A | 6/1992 | Andrews |
| 5,184,617 | A | 2/1993 | Harris et al. |
| 5,330,515 | A | 7/1994 | Rutecki et al. |
| 5,330,527 | A | 7/1994 | Montecalvo et al. |
| 5,350,414 | A | 9/1994 | Kolen |
| 5,562,707 | A | 10/1996 | Prochazka et al. |
| 5,597,309 | A | 1/1997 | Riess |
| 5,814,093 | A | 9/1998 | Stein |
| 5,895,416 | A | 4/1999 | Barreras, Sr. et al. |
| 5,961,542 | A | 10/1999 | Agarwala |
| 5,964,789 | A | 10/1999 | Karsdon |
| 6,016,449 | A | 1/2000 | Fischell et al. |
| 6,044,303 | A | 3/2000 | Agarwala et al. |
| 6,066,163 | A | 5/2000 | John |
| 6,083,156 | A | 7/2000 | Lisiecki |
| 6,094,598 | A | 7/2000 | Elsberry et al. |
| 6,246,912 | B1 | 6/2001 | Sluijter et al. |
| 6,356,784 | B1 | 3/2002 | Lozano et al. |

FOREIGN PATENT DOCUMENTS

| | | |
|---|---|---|
| EP | 0911061 | 4/1999 |
| WO | WO 90/12293 | 10/1990 |
| WO | WO 97/39795 | 10/1997 |
| WO | WO/97/39796 | 10/1997 |

OTHER PUBLICATIONS

Berg, et al. "Measuring balance in elderly: preliminary development of an instrument," *Physio-therapy* Canada. 1989;41:304-311.

Brown et al., "Action tremor and weakness in Parkinson's disease: a study of the elbow exensors," *Mov. Disord.*, Jan. 1998, 13(1), 56-60.

Brown, "Cortical drives to human muscle: the Piper and related rhythms," *Prog. Neurobiol.*, Jan. 2000, 60(1), 97-108.

Brown et al., "Does parkinsonian action tremor contribute to muscle weakness in Parkinson's disease?" *Brain*, Mar. 1997, 120 (Pt.3), 401-8.

Brown, "Muscle sounds in Parkinson's disease," *Lancet*, Feb. 22, 1997, 349(9051), 533-5.

Burleigh-Jacobs et al., "Step initiation in Parkinson's disease: influence of levodopa and external sensory triggers," *Mov Disord* Mar. 1997;12(2):206-15.

Choi et al., "Selectivity of Multiple-Contact Nerve Cuff Electrodes: A Simulation Analysis," *IEEE Transactions of Biomedical Engineering*, 48(2); Feb. 2001, 165-172.

Dinnerstein et al., "Delayed feedback as a possible mechanism in parkinsonism," *Percept Mot Skills* 1962;15:667-80.

Ebersbach et al., "Interference of rhythmic constraint on gait in healthy subjects and patients with early Parkinson's disease: evidence for impaired locomotor pattern generation in early Parkinson's disease," *Mov Disord* Jul. 1999;14(4):619-25.

Enzensberger et al., "Metronome therapy in patients with Parkinson's disease," *Nervenarzt* Dec. 1997;68(12):972-7.

FDA (Food and Drug Administration). Guidance Document for Powered Muscle Stimulator 510(k)s. Jun. 9, 1999.

Freedland et al., "The effects of pulsed auditory stimulation on various gait measurements in persons with Parkinson's Disease," *NeuroRehabilitation* 2002;17(1):81-7.

Gilman, "Joint position sense and vibration sense: anatomical organization and assessment," *J Neurol Neurosurg Psychiatry* 2002;73:473-477.

Glickstein, "Paradoxical movement in Parkinson's disease," *TINS*,14,480-482, 1991.

Guyton et al., Textbook of Medical Physiology 2000, Coverpage, Copyright Page, and Table of Contents, 22 pp.

Hallet, "Classification and treatment of tremor," *JAMA*, Aug. 28, 1991 v266 n8 p. 1115(3).

Horak et al., "Effects of dopamine on postural control in parkinsonian subjects: scaling, set, and tone," *J Neurophysiol* 1996;75:2380-96.

Jobst et al. "Sensory perception in Parkinson disease," *Arch Neurol* 1997;54:450-4.

Johnson et al., "Modulation of the stretch reflex during volitional sinusoidal tracking in Parkinson's disease.," *Brain* Feb. 1991;114 ( Pt 1B):443-60.

Kaczmarek et al., "Maximal Dynamic Range Electrotactile Stimulation Waveforms," *IEEE Trans. Biomed. Eng.* Jul. 1992 vol. 39, No. 7.

Kandel et al., *Essentials of Neural Science and Behavior* 1995, Cover Page, Copyright Page, and Table of Contents, 11 pp.

Kantor et al., "Phase charge significance in peripheral nerve excitation with constant voltage and constant current stimulation," *Proceedings of the 15th Annual International Conference of the IEEE-EMBS*, 1993:1255-1256.

Kantor et al., "The effects of selected stimulus waveforms on pulse and phase characteristics at sensory and motor thresholds," *Phys Ther* Oct. 1994;74(10):951-62.

Kantor et al., "Effects Of Electrode Size On Basic Excitatory Responses And Selected Electric Stimulator Parameters," vol. 14, *Proceedings of the Annual International Conference of the IEEE-EMBS*, vol. 6 , Oct. 29-Nov. 1, 1992: 2318-2319.

Kingsley, Concise Text of Neuroscience 2000, Coverpage, Copyright Page, and Table of Contents, 3 pp.

Klockgether et al., "A defect of kinesthesia in Parkinson's disease," *Mov Disord* 1995;10:460-5.

Lee et al., "Motor responses to sudden limb displacements in primates with specific CNS lesions and in human patients with motor system disorders," *Can J Neurol Sci* Aug. 1975;2(3):285-93.

Llinas et al., "A neurological and neuropsychiatric syndrome characterized by magnetoencephalography," *Proc Natl Acad Sci* 1999; vol. 96 No. 26:15222-15227.

Marchese et al., "The role of sensory cues in the rehabilitation of parkinsonian patients: a comparison of two physical therapy protocols," *Mov Disord* Sep. 2000;15(5):879-83.

Martin, "The basal ganglia and posture," London: Pitman, 1967, Cover Page, Copyright Page, Table of Contents, 4 pp.

McAuley et al., "Levodopa reversible loss of the Piper frequency oscillation component in Parkinson's disease," *J Neurol Neurosurg Psychiatry* Apr. 2001;70(4):471-6.

Moore, "Impaired sensorimotor integration in parkinsonism and dyskinesia: a role for corollary dischaaarges?" *J Neurol Neurosurg Psychiatry*, 1987;50:544-52.

Morris et al., "Ability to modulate walking cadence remains intact in Parkinson's Disease," *J Neurology, Neurosurgery, and Psychiatry* 1994; 57:1532-1534.

Morris et al., "The pathogenesis of gait hypokinesia in Parkinson's Disease," *Brain* Oct. 1994;117 (Pt 5):1169-81.

O'Suilleabhain et al., "Proprioception in Parkinson's disease is acutely depressed by dopaminergic medications," *Journal of Neurology, Neurosurgery and Psychiatry*, Nov. 2001; v71 i5, p. 607.

Patterson et al., "The influence of electrode size and type on surface stimulation of the quadriceps," *IEEE Trans. On Rehab. Eng.*, Mar. 1993; v1 i1, p. 59.

Piper, Elektrophysiologie menschlicher Muskeln. Berlin: Springer: 1912; Riley, *Electrical Stimulation and Electropathology*, Cambridge University Press, 1992.

Popovic et al., Surface-Stimulation Technology for Grasping and Walking Neuroprostheses, *IEEE Engineering in Medicine and Biology*, Jan./Feb. 2001; 82-93.

Prochazka et al., "Attenuation of pathological tremors by functional electrical stimulation—I: Method," *Ann. Biomed. Eng.*, vol. 20, pp. 225-236, 1992.

Reilly, JP. Electrical Stimulation and Electropathology, Cambridge University Press, 1992; Cover Page, Copyright Page, and Table of Contents, 9 pp.

Riess et al., "Augmented Reality and Parkinson's Disease," 2 pgs.; http://ftp.hitl.washington.edu/publications/r-99-5/; Jan. 22, 2002.

Rocchi et al., "Effects of deep brain stimulation and levadopa on postural sway in Parkinson's Disease," *Journal of Neurology, Neurosurgery and Psychiatry*, 2002;73:267-274.

Smithson et al., "Performance on clinical tests of balance in Parkinson's disease," *Phys Ther*, Jun. 1998;78(6):577-92.

Thaut, et al., "Rhythmic auditory stimulation in gait training for Parkinson's disease patients," *Mov Disord*, Mar. 1996;11(2):193-200.

Timmerman et al., "The cerebral oscillatory network of parkinsonian resting tremor," *Brain* 2003, 126:199-212.

Volkmann et al., "Central motor loop oscillations in parkinsonian resting tremor revealed by magnetoencephalography," *Neurology* 1996; 46:1359-1370.

Zia et al., "Joint position sense is impaired by Parkinson's disease," *Ann Neurol*, 2000;47:218-28.

Hildick-Smith, M., "Pragmatic physical therapy in Parkinson's disease: Any scientific basis?", in Stern GM (ed): "Parkinson's Disease: Advances in Neurology", 1999, pp. 561-564, vol. 80, Publisher: Lippincott Williams and Wilkins, Published in: Philadelphia, US.

IANSEK, Robert, "Interdisciplinary Rehabilitation in Parkinson's Disease", in Stern GM (ed): "Parkinson's Disease: Advances in Neurology", 1999, pp. 561-564, vol. 80, Publisher: Lippincott Williams and Wilkins, Published in: Philadelphia, US.

SYSTEMS AND METHODS FOR TREATING MOVEMENT DISORDERS

CROSS REFERENCE TO RELATED APPLICATIONS

This application is related to and claims the benefit of the filing date of now abandoned provisional application Ser. No. 60/420,769 (the '769 Application), filed on Oct. 24, 2002. The '769 Application is incorporated by reference.

This application is related to copending applications U.S. Ser. No. 09/659,351 (the '351 Application), entitled Adaptive Stimulator for Relief of Symptoms of Neurological Disorders, filed on Sep. 12, 2000 and U.S. Ser. No. 10/005,458 (the '458 Application), entitled Movement Timing Stimulator, filed on Nov. 2, 2001. The '351 and '458 applications are incorporated herein by reference.

TECHNICAL FIELD

The present invention relates to systems and methods for treating movement disorders. In particular, the present invention relates to systems and methods for relieving symptoms of Parkinson's disease.

BACKGROUND

A movement disorder is a neurological disturbance that involves one or more muscles or muscle groups. Movement disorders include Parkinson's disease, Huntington's Chorea, progressive supranuclear palsy, Wilson's disease, Tourette's syndrome, epilepsy, and various chronic tremors, tics and dystonias. Different clinically observed movement disorders can be traced to the same or similar areas of the brain.

Parkinson's Disease (PD) is a neurodegenerative disorder that affects approximately one percent of the population over age 50 and up to two and a half percent of the population over age 70. The hallmarks of the disease are its motor features—resting tremor, rigidity, and akinesia/bradykinesia (inability to initiate movement and slowness of movement, respectively) and postural instability. These hallmark features result in gait and postural disturbances that impair performance during everyday tasks, such as walking, cooking, eating, personal hygiene and exercise.

Gait abnormalities in PD are characterized by start hesitation, freezing, festination, reduced stride length and reduced velocity. The preferred walking speed is much lower for PD patients, as compared to controls, and this deficit can be accounted for by reduced stride length. (Morris, et al, 1994).

PD is characterized by movement dysfunction resulting from selective neurodegeneration of dopamine producing neurons of the substantia nigra pars compacta (SNpc). Accordingly, the mainstay of therapy involves pharmacologic interventions that replace dopamine, such as, levodopa and dopamine agonists. Surgical interventions, such as pallidotomy or deep brain stimulation (DBS) have been employed when symptoms can no longer be effectively treated with medication. Interestingly, postural instability improved with DBS in one small (n=6) study while instability was exacerbated by levodopa (Rocchi, et al, 2002).

While treatments for PD are primarily pharmacological, studies examining basal ganglia dysfunction in PD have led to the development of physical rehabilitative approaches for the treatment of motor symptoms, especially those related to the initiation and timing of motor acts (lansek, 1999). For example, one notable feature of PD is that the deficits associated with akinesia and bradykinesia are more pronounced during self-initiated actions in contrast to stimulus-initiated movements. The common scenario of 'paradoxical kinesia', where PD patients can move normally with correct external sensory cueing, is empirical evidence that even PD patients with advanced disease have the potential to execute normal movements (Glickstein & Stein, 1991).

Auditory cues have been successfully employed for physical therapy and home based gait training (Freedland, et al, 2002; Enzensberger, et al, 1997; Morris, et al, 1994; Thaut, et al, 1996; Marchese, et al, 2000). Interestingly, periodic patterns of 0.625 hertz were most effective. Visual and electrical cutaneous cues have also been employed to improve gait and to initiate movement ((Morris, et al, 1994; Burleigh-Jacobs, et al, 1997). Patients frequently alleviate symptoms using external visual and auditory cues. These may include verbal commands given by a caregiver, auditory cues from a metronome, visual cues from laser pointers or floor tile patterns or the placement of masking tape at equally spaced intervals to serve as a visual target for enhancement of stride. These non-pharmacological areas, however, remain in their infancy. Despite the use of physical therapies and other adaptive "tricks" by PD patients, there is a crucial need for systematic development of evidence-based physical treatments that will complement pharmacological (as well as neurosurgical) treatment strategies (Hildick-Smith, 1999).

Postural stability is impaired in PD with abnormal postural sway in stance, reduced compensating force production in response to external perturbation, and higher tonic EMG background activity. Treatment with levodopa has been show to actually increase postural sway in the mediolateral direction (Rocchi, et al, 2002). This effect on postural sway, and, hence, postural instability, may not be detected ordinarily in clinical assessments of antiparkinsonian treatments since postural stability in this direction is not evaluated in the Unified Parkinson Disease Rating Scale (UPDRS) (Fahn & Elton, 1987), the accepted clinical scale for rating motor deficits in PD. PD patients fail to produce adequate force to compensate for large amplitude translational perturbations. These deficits are also accompanied by improper bursting of the antagonist muscle and increased tonic background activity (Horak et al, 1996).

Postural instability and gait abnormalities may also be influenced by a hyper stretch reflex. PD patients demonstrate a centrally mediated hyper long latency stretch reflex to both passive and volitional reaction to an external displacement (Lee & Tatton, 1975; Johnson, et al, 1991). It has been suggested that this abnormal reflex may have a role in reducing stride length and force production, by truncating the action of the agonist while facilitating the antagonist.

Further, magnetoencephalography (MEG) analysis has shown cortical oscillation at tremor frequency and double tremor frequency continuously present in the PD cortex (Volkmann, et al, 1996; Llinas, et al, 1999; Timmerman, et al, 2003). These oscillations do not always present themselves as rest tremor upon clinical exam and it has been suggested that they may have a role in bradykinesia by forcing movement to synchronize and fit within the temporal window of these oscillations. Thus, large amplitude excursions would be truncated at the start of the next tremor cycle limiting range of motion and force production. These oscillations may also be responsible for bursting seen in quiet stance EMGs.

Habituation is often a problem with conventional transcutaneous stimulation resulting in a reduction of perceived stimulation intensity. Conventional techniques used to minimize this habituation include bi-phasic stimulation pulses and amplitude modulation of the pulse. Amplitude modulation provides a pulse that appears to change in intensity; thus, the CNS continues to attend to this changing intensity. Lower pulse repetition rates (higher pulse periods) also reduce susceptibility to habituation. Conventional transcutaneous stimulation periods are typically 5-10 milliseconds.

For the reasons stated above, and for other reasons stated below which will become apparent to those skilled in the art upon reading and understanding the present specification, there is a need in the art for improvements in techniques to provide patients affected with neurological movement disorders relief from the symptoms.

SUMMARY

The above-mentioned problems with treatment of the symptoms of neurological movement disorders and other problems are addressed by embodiments of the present invention and will be understood by reading and studying the following specification.

A method of improving a patient's gait is provided. The method includes producing a plurality of stimulation prompts at a plurality of stimulation points using multiple stimulation channels, applying the plurality of stimulation prompts in a timed periodic fashion across the plurality of stimulation points, and activating a return electrode whenever one of the multiple stimulation channels on an associated leg is active. The plurality of stimulation points is located symmetrically on each leg. The plurality of stimulation prompts are not synchronized with the patient's gait. Each of the multiple stimulation channels is associated with a stimulation electrode at one of the plurality of stimulation points.

A method of relieving postural instability for an individual is provided. The method includes producing a plurality of stimulation prompts at a plurality of stimulation points using multiple stimulation channels, applying the plurality of stimulation prompts in a timed periodic fashion across the plurality of stimulation points, and activating a return electrode whenever one of the multiple stimulation channels on an associated leg is active. The plurality of stimulation points is located symmetrically on both legs. Each of the multiple stimulation channels is associated with a stimulation electrode at one of the plurality of stimulation points. The plurality of stimulation points is associated with a plurality of muscles and contraction of the plurality of muscles is not coincident with the corresponding stimulation prompt.

A method of improving arm swing is provided. The method comprising includes producing a plurality of stimulation prompts at a plurality of stimulation points using multiple stimulation channels, applying the plurality of stimulation prompts in a timed periodic fashion across the plurality of stimulation points, and activating a return electrode whenever one of the multiple stimulation channels is active. The plurality of stimulation points is located to prompt arm swing. The plurality of stimulation prompts are not synchronized with the arm swing. Each of the multiple stimulation channels is associated with a stimulation electrode at one of the plurality of stimulation points.

A movement timing stimulator system for the treatment of symptoms of Parkinson's Disease is provided. The system including one or more motion sensors adapted to detect one or more movement parameters of a patient, a control panel, a plurality of customized parameter setting menu, and an over voltage/current monitoring circuit. The system further includes a controller that receives signals from the one or more motion sensors, control panel, customized parameter setting menus, and monitoring circuit and determines when stimulation prompts are required for a desired treatment of symptoms and a plurality of cutaneous stimulation electrodes placed in the vicinity of motor points for timed periodic stimulation prompts, wherein the stimulation prompts are sequentially applied based on the desired treatment of symptoms. The plurality of stimulation prompts is produced using multiple stimulation channels and each stimulation channel is associated with a cue clock. The stimulation prompts are not synchronized with a patient's movement. The system further includes at least one return electrode coupled to each of the plurality of stimulation electrodes.

A method of reducing tremor for individuals having a movement disorder is provided. The method includes producing a plurality of stimulation prompts at a plurality of stimulation points using multiple stimulation channels, applying the plurality of stimulation prompts in a timed periodic fashion across the plurality of stimulation points, and activating a return electrode whenever one of the multiple stimulation channels is active. The plurality of stimulation points is located to reduce arm tremor. The plurality of stimulation prompts are not synchronized with the tremor. Each of the multiple stimulation channels is associated with a stimulation electrode at one of the plurality of stimulation points.

DETAILED DESCRIPTION

In the following detailed description, reference is made to the accompanying drawings that form a part hereof, and in which is shown by way of illustration specific illustrative embodiments in which the invention may be practiced. These embodiments are described in sufficient detail to enable those skilled in the art to practice the invention, and it is to be understood that other embodiments may be utilized and that logical, mechanical and electrical changes may be made without departing from the spirit and scope of the present invention. The following detailed description is, therefore, not to be taken in a limiting sense.

A noninvasive system for relieving bradykinesia and tremor in Parkinson's disease (PD) is disclosed. The system uses multi-channel electrical or mechanical stimulation prompts to facilitate movement in PD. In one embodiment, the system consists of a stimulation device with robust configurable parameters and the application methods for efficacy. In one embodiment, stimulation prompts are empirically derived timing patterns that have been demonstrated to alleviate symptoms of Parkinson's disease. Unlike previous systems (Prochazka U.S. Pat. No. 5,562,707), the stimulation does not force muscle contraction and is not synchronized with the movement.

Embodiments of the present invention provide a logical approach of externally augmenting sensory perception to compensate for impaired proprioception. In one embodiment, cutaneous electrical stimulation is used as a prompt for movement disorders. The application of periodic external stimulation prompts aids in restoring near normal movement. Embodiments of the present invention provide methods and systems of relieving PD symptoms through application of static or adaptive cutaneous electrical or mechanical stimulation applied to torso, limbs and extremities. In one embodiment, this therapy influences proprioception through stimulation of muscle spindle afferents and cutaneous and subcutaneous mechanoreceptors or afferents. In one embodiment, electrical stimulation of Golgi tendon and muscle spindle afferents affects the muscle stretch reflex of the stimulated muscle and through reciprocal innervation the fusimotor drive of the myotatic unit.

In one embodiment, cutaneous stimulation acts as a movement cue similar to visual or auditory cues. In some embodiments, it also reduces the stiffness of the myotatic unit through muscle spindle afferents and inter-neurons while facilitating muscle contraction through the central nervous system. By facilitating agonist muscle contraction while inhibiting the antagonist through reciprocal inter-neurons, stimulation enables a more normal muscle stretch reflex. By applying stimulation in a timed periodic fashion across electrodes or transducers to stimulation points on the limb, the patient is presented with a pattern that is used to initiate and time movement. In some embodiments, rather than synchronizing with the cues, the patient uses the pattern to develop individualized timing.

Embodiments of the present invention provide relief of PD symptoms including bradykinesia, rigidity, tremor, and postural instability through the application of topically applied sensory stimulation prompts at a plurality of stimulation points. Embodiments of the present invention also provide treatment as an intervention for neuropathy.

Figure 1:
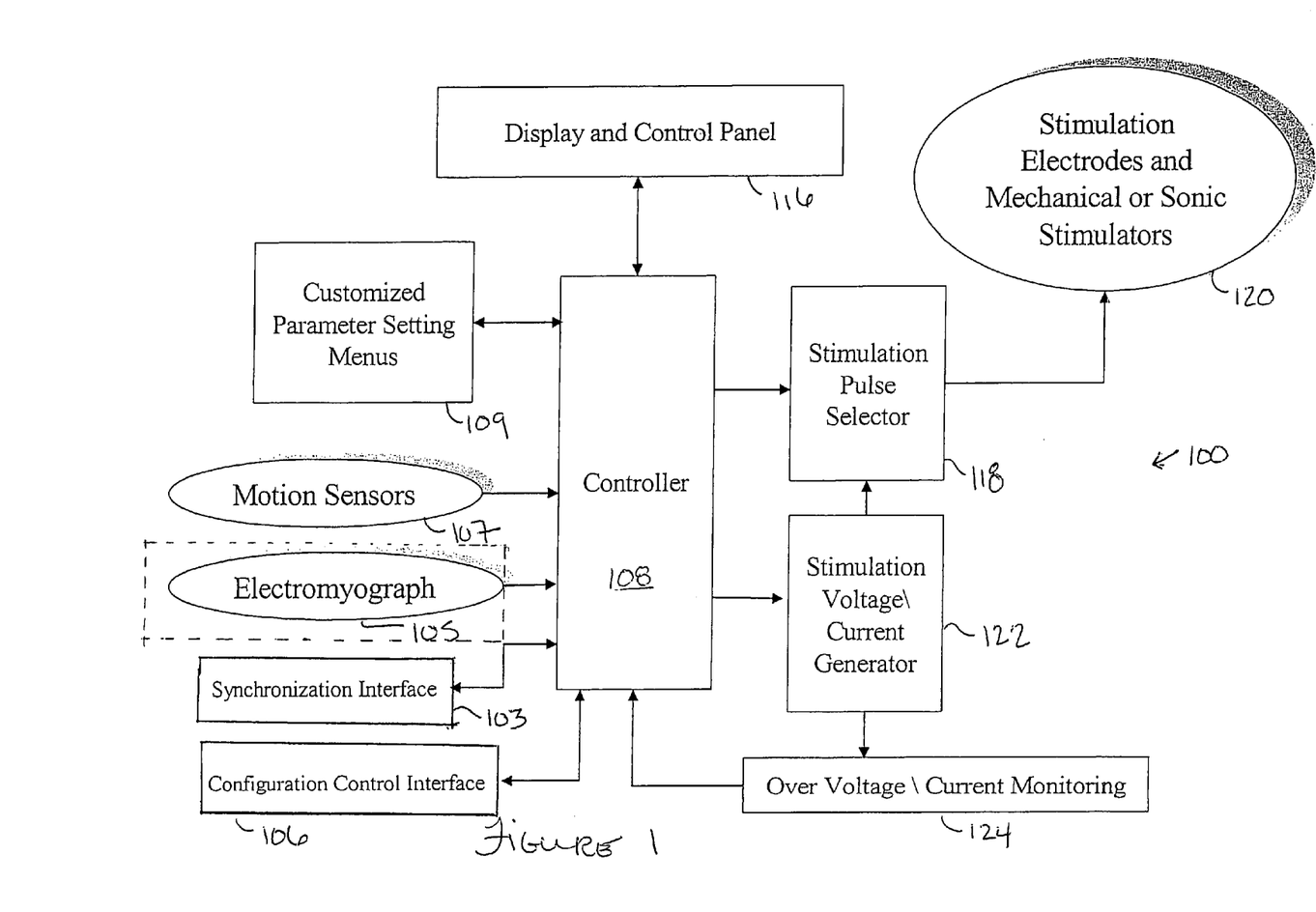
FIG. 1 is a block diagram of an embodiment of a movement timing stimulation system according to the teachings of the present invention.

FIG. 1 is a block diagram of one embodiment of a movement timing stimulator (MTS) system shown generally at 100 according to the teachings of the present invention. In one embodiment, movement timing stimulator system 100 is battery operated. System 100 includes a controller 108 that receives data from one or more sensors 107. In one embodiment, sensor 107 is a motion sensor such as a tri-axial accelerometer or the like. In one embodiment, sensor 107 adapted to detect one or more movement parameters of a patient, lack of movement, acceleration, deceleration, and the like. In another embodiment, sensors 107 are as described in copending application U.S. Ser. No. 09/659,351 (the '351 Application), entitled Adaptive Stimulator for Relief of Symptoms of Neurological Disorders, filed on Sep. 12, 2000. In another embodiment, sensors 107 are as described in copending application U.S. Ser. No. 10/005,458 (the '458 Application), entitled Movement Timing Stimulator, filed on Nov. 2, 2001. In one embodiment, MTS 100 is as described in the '458 Application. In an alternate embodiment, MTS 100 is as described in the '351 Application.

Controller 108 is the central control element of MTS system 100. In one embodiment, controller 108 is a low-power microcontroller. In another embodiment, controller 108 receives data from electromyograph 105. In an alternate embodiment, controller 108 receives data from both one or more motion sensors 107 and electromyograph 105. Controller 108 uses the data to control stimulation pulse selector 118 and stimulation voltage/current generator 122 to produce signals for transmission to stimulation electrodes and/or stimulators 120. In one embodiment, electrodes 120 include one or more stimulation electrodes and return electrodes. In one embodiment, one or more of the stimulation electrodes are electrical, mechanical and/or sonic stimulators and provide a plurality of stimulation prompts at a plurality of stimulations points using multiple stimulation channels. In one embodiment, controller 108 monitors stimulation electrode current and applied voltage for each stimulation pulse. In one embodiment, controller 108 monitors power to ensure that electrode power density is not exceeded per FDA specifications (FDA, 1999).

In operation, stimulation is provided by electrical currents applied through stimulation electrodes 120. In another embodiment, stimulation is provided by pressure waves produced by stimulation electrodes 120. In one embodiment, stimulation electrodes 120 are mechanical vibrators or sonic transducers. In one embodiment, current for the stimulation prompts is approximately 10 milliamps.

In operation, controller 108 generates the basic timing for stimulation waveforms that are used for stimulation prompts. Controller 108 also adjusts frequency, pulse-width, waveform shape, and amplitude based on sensor information and/or operator controls. For electrical stimulation, controller 108 also monitors stimulation electrode voltage and current, via over voltage/current monitoring circuit 124, to prevent exposure of the patient to uncomfortable stimulation levels. Controller 108 processes information from input signals received from display and control panel 116, customized parameter setting menus 109, motion sensors 107, electromyograph 105, synchronization interface 103, configuration control interface 106, over voltage/current monitoring circuit 124 or the like. In one embodiment, an individual wearing the device may adjust the controls to a comfortable level via control panel 116. Other parameters may be adjusted from control panel 116, a laptop computer or personal digital assistant via configuration control interface 106. Software embedded in system 100 performs adaptation of stimulation by stimulation electrodes 120. In operation, one or more motion sensors 107 are interrogated by controller 108 and the information is used to provide compensating stimulation signals. In one embodiment, stimulation prompts may be in the form of cutaneous electrical or vibration stimulation provided by one or more mechanical or sonic transducers. In another embodiment, electromyograph 105 uses electromyography to detect bursting in the EMG.

In one embodiment, stimulation voltage/current generator 122 produces the individual stimulation signals. In one embodiment, generator 122 is a constant voltage type with programmable current limiting. In one embodiment, voltage is also adjusted by controller 108. In operation, by adjusting the value of the current limit, system 100 can effectively be used as a constant current or constant voltage source.

In operation, synchronization interface 103 provides central clock synchronization allowing coordinated stimulation across multiple systems such as system 100. In one embodiment, at the beginning of each stimulation cycle, a short high frequency burst of low amplitude pulses are applied through stimulation electrodes 120. In one embodiment, this burst is decoded by each system 100 and used as a start marker for each stimulation cycle.

In operation configuration control interface 106 is an external computer interface that allows control of device parameters. In one embodiment, configuration control interface 106 is implemented as one of a wired, infrared or wireless link.

In one embodiment, stimulation pulse selector 118 time division multiplexes the stimulation pulse to each stimulation channel. It is understood that other transmission techniques may be used instead of time division multiplexing.

A stimulation channel may be selected as a stimulation output or as a return for a stimulation channel. Thus, many stimulation channels may share common return channels or stimulation channels may be paired. Pulses may be passed as either positive or negative going pulses; thus, mono-phasic, alternating phase and bi-phasic waveforms are supported. Stimulation signals are phased as non-overlapping pulses, preventing unwanted cross coupling of currents between stimulation electrodes when electrical stimulation is used.

In operation, in one embodiment, the return electrode surface area is about 3 times the area of a given stimulation channel electrode. This results in a higher current density in the stimulation electrode. The perceived stimulation at the stimulation electrode site is thus larger than the return electrode site. Therefore, the prompt is perceived at the stimulation electrode versus the return electrode site. Since the duty cycle is much higher for the return electrode, the larger surface area and associated reduction in current density also reduces the risk of skin irritation.

Table 1 includes a number of amplitude and current programmable parameters and their functional description for system 100.

TABLE 1

Amplitude and Current Programmable Parameters and Function

| Parameter | Functional Description |
|---|---|
| Pulse Amplitude | The global amplitude level for each stimulation pulse. This may be adjusted through the front panel control. |
| Amplitude Modulation | Enables ramp of the amplitude over a given modulation interval. Ramp refers to the linear increase in pulse amplitude from "0" to the amplitude control setting over the modulation interval. At the end of the increasing interval the amplitude is ramped back to "0" over the same interval length. The cycle is then repeated. |
| Binary Modulation | Enables binary amplitude modulation over a given modulation interval. Binary amplitude modulation refers to alternating the pulse amplitude between 0.5X and 1.0X over consecutive modulation intervals. "X" refers to the value of the amplitude control setting. |
| Amplitude Modulation Interval | The interval over which ramp or binary amplitude modulation is applied to the stimulation pulse. |
| Stimulation pulse current limit | The current limit to which the stimulation pulse is clamped on any given channel. |
| Stimulation pulse current limit delta [n] | A delta current limit value for each channel that in conjunction with the stimulation current limit allows a custom current limit for each channel [n]. |
| Pair-wise | Enables channels 1/2, 3/4, 5/6 and return electrode 1/return electrode 2 to operate paired such that current flows only between the electrode pairs. |
| Return Select [n] | Selects common return 1 or common return 2 as the common return for each channel [n]. |

Table 2 includes a number of frequency related programmable parameters and their function description for system 100.

TABLE 2

Frequency Related Programmable Parameters and Function

Figure 2:
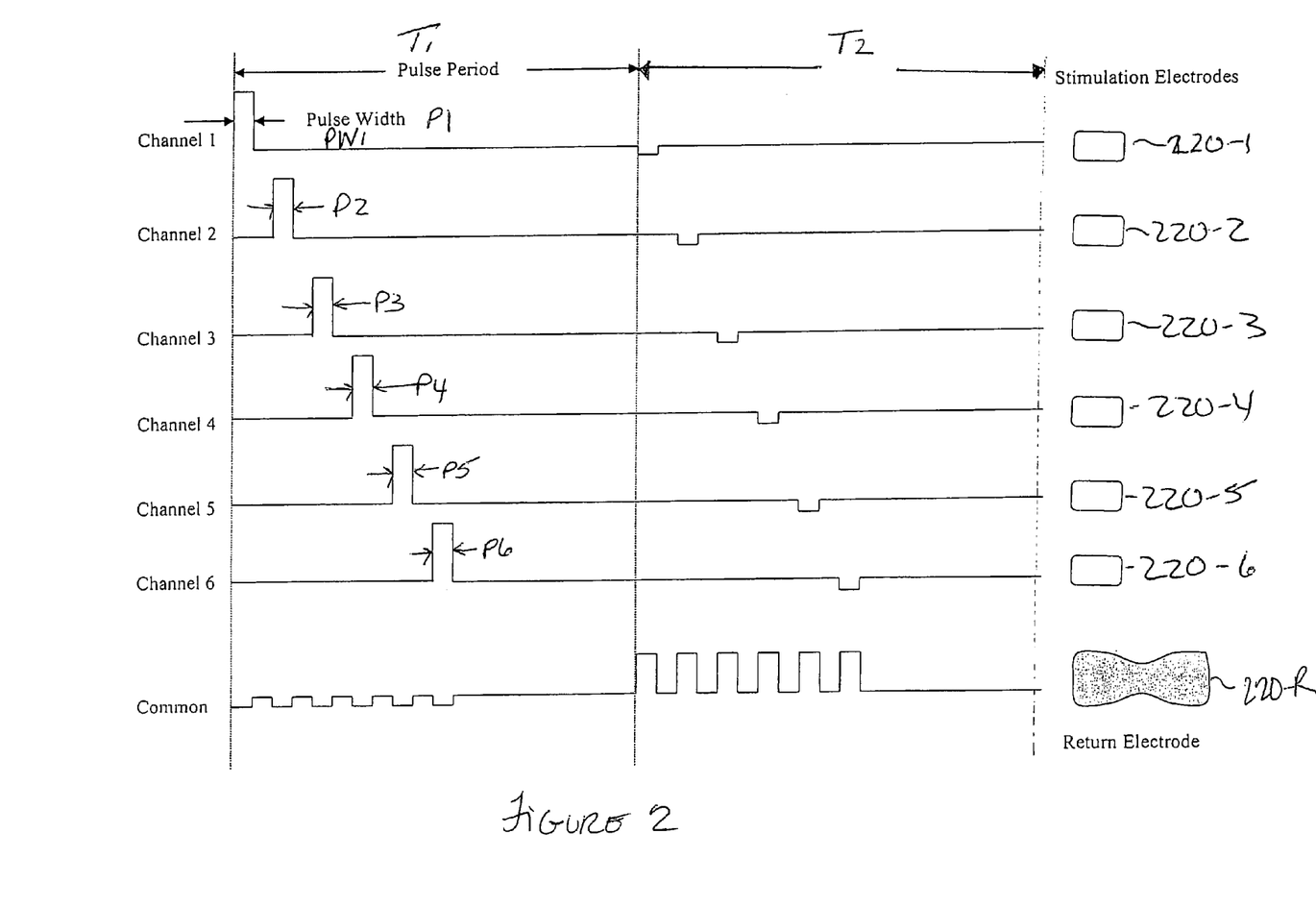
FIG. 2 is an illustration of one embodiment of stimulation pulses for a movement timing stimulation system according to the teachings of the present invention.
Figure 3:
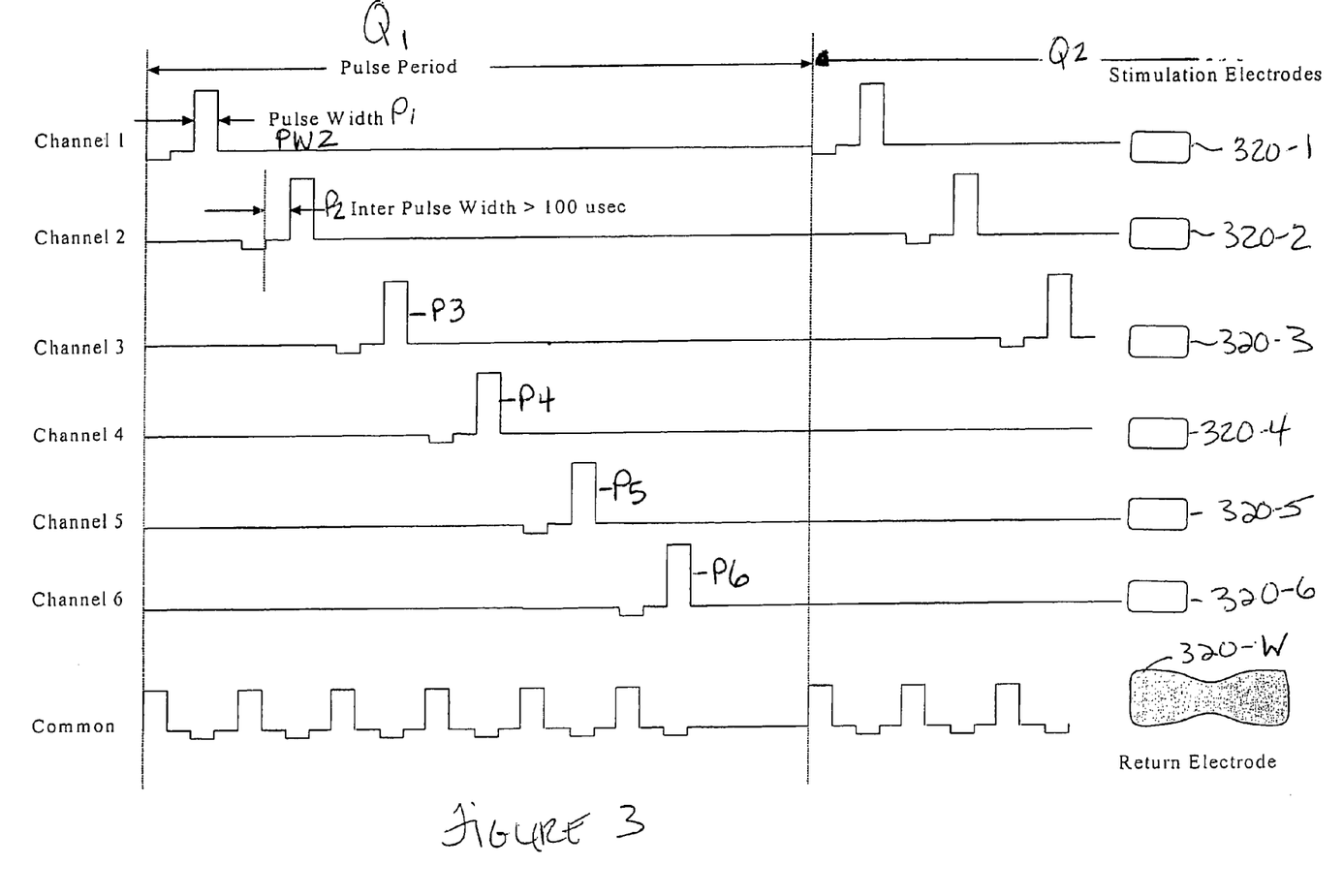
FIG. 3 is an illustration of one embodiment of a biphasic stimulation pulse for a movement timing stimulation system according to the teachings of the present invention.
Figure 4:
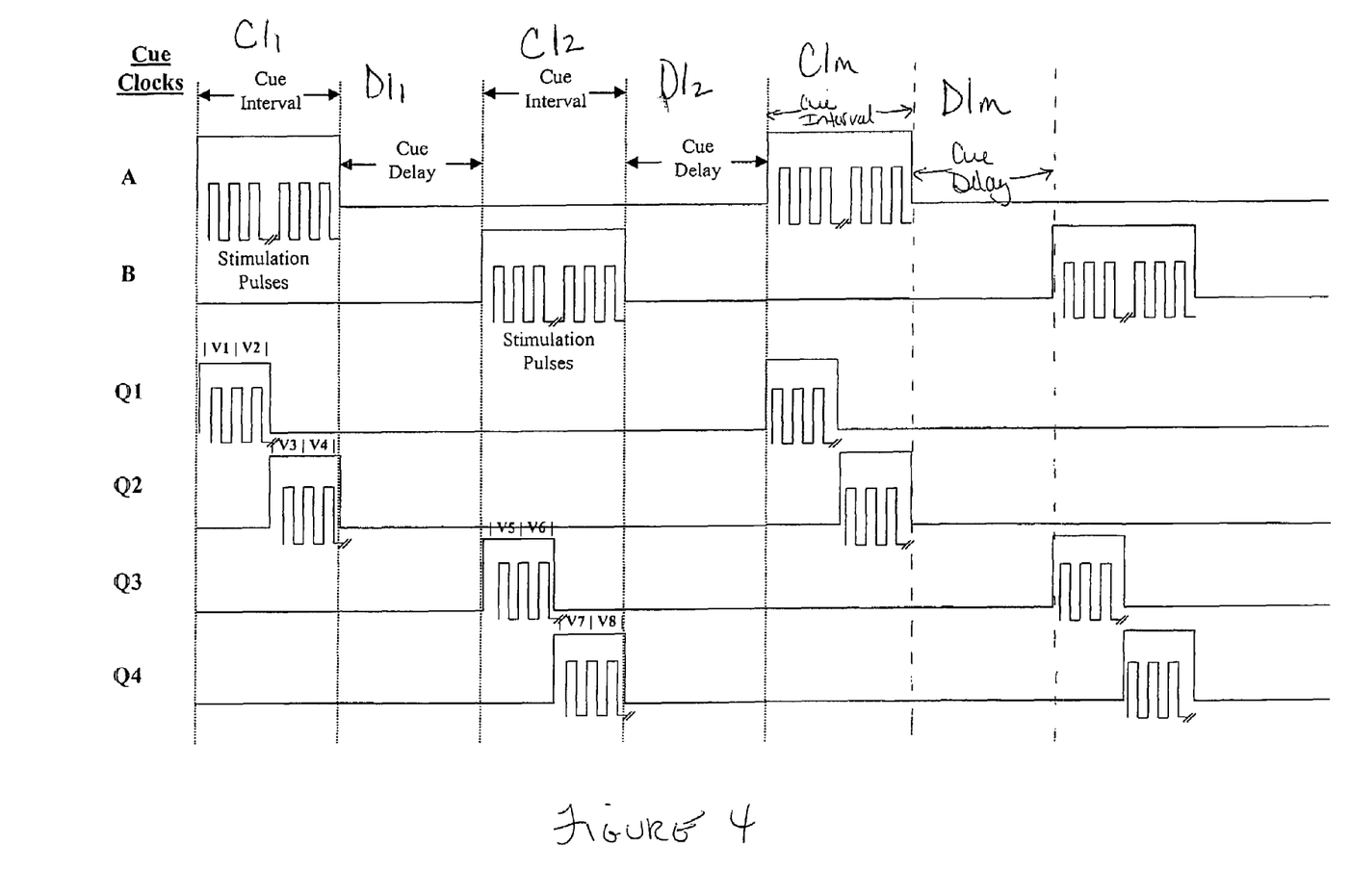
FIG. 4 is an illustration of one embodiment of cue clocks for use with a movement timing stimulator according to the teachings of the present invention.

| Parameter | Functional Description |
|---|---|
| Stimulation pulse period | The number of milliseconds between stimulation pulses on any given channel. As shown in FIG. 2 for alternating phase, pulse period is measured from the rising edge of the first pulse to the falling edge of the pulse for the next cycle. As shown in FIG. 3 for bi-phasic pulses, pulse period is measured from the falling edge of the first pulse to the falling edge of the pulse for the next cycle. |
| Frequency Modulation Delta | Enables ramp of stimulation pulse period over a given modulation interval. Ramp refers to the linear increase in stimulation pulse period from (stimulation pulse period − modulation delta) to the (stimulation pulse period + modulation delta) over the modulation interval. At the end of the increasing interval the stimulation pulse period is ramped back to (stimulation pulse period − modulation delta) over the same interval length. The cycle is then repeated. This method provides frequency modulation of the stimulation pulse. |
| Frequency Modulation Interval | The interval over which frequency modulation is applied to the stimulation pulse. |
| Random Frequency Modulation | Enables random modulation of the stimulation pulse period. The Frequency Modulation Delta is used to set the upper and lower limits of the modulation. The Frequency Modulation Interval sets the rate at which the frequency changes. |
| Stimulation pulse width | The number of microseconds for which the stimulation pulse activates on any given channel. As shown in FIG. 2 for alternating phase, pulse width is measured from the rising edge of the first pulse to the falling edge of the same pulse. As shown in FIG. 3 for bi-phasic pulses, pulse width is the same for the negative going and positive going pulses within the same cycle. |
| Stimulation pulse width delta [n] | A delta stimulation pulse width value for each channel that in conjunction with the stimulation pulse width allows a custom pulse width for each channel [n]. |
| Polarity and Burst | Allows the selection of negative going, positive going, alternating polarity (FIG. 2) or biphasic polarity (FIG. 3) stimulation pulses. Also allows selection of a burst count for the number of pulses in each burst cycle. |
| Burst count delta [n] | A delta burst count value for each channel that in conjunction with the burst count allows a custom burst count for each channel [n]. |
| Burst Modulation | Allows the selection of modulation of the burst count. The modulation value is also specified which is summed with the global burst count |
| Burst Modulation Interval | The interval over which burst modulation is applied to the stimulation pulse. |
| Stimulation cue interval | The number of seconds for which the stimulation pulse is enabled on any given channel as shown in FIG. 4. Note that the number of stimulation pulses that actually occur during this interval is dependent upon the stimulation pulse period and the burst count. |
| Stimulation cue delay interval | The number of seconds between the end of the last cue interval and the start of the next cue interval as shown in FIG. 4. |
| Random cue delay | Enables random delays between stimulation cues. The stimulation cue delay interval is used as the maximum delay. This is effectively random frequency modulation of the cue clocks. |

FIG. 2 is an illustration of one embodiment of stimulation pulses for a movement timing stimulation system such as system 100 of FIG. 1. In one embodiment, the waveforms of FIG. 2 are applied to an electrical stimulation system. In another embodiment, the waveforms are applied to a pressure stimulation system. Although FIG. 2 illustrates 6 channels the discussion may be applied to a system having any number of channels.

In this embodiment, an MTS system such as system 100 provides synchronized electrical stimulation through topically applied electrodes 220-1 to 220-6 across up to 6 stimulation channels and two return channels. In one embodiment, over a given pulse period $T_1$ each channel is sequentially pulsed. The pulse period $T_1$ is the same for each channel, albeit offset in time from the other channels. In one embodiment, the pulse width $P_{w1}$ is the same for each channel. In an alternate embodiment, the pulse widths P1 to P6 are independently adjusted for each channel. This will be further discussed below with respect to FIG. 3. In operation, on any given channel, the pulse polarity may alternate between sequential pulses as shown in FIG. 2. In this embodiment, the pulses alternate polarity on every other pulse. In this embodiment, channel 1 starts with a positive going pulse during pulse period $T_1$ and a negative going pulse during period $T_2$.

In operation, in one embodiment all stimulations channels use one of two common return channels. One stimulation electrode 220-1 to 220-6 and one return electrode 220-R are active at any given time providing current flow between these electrodes. Since only one stimulation electrode 220-1 to 220-6 is active at any given time; no current flows between stimulation electrodes 220-1 to 220-6. When no stimulation pulse is active on a given channel, the channel floats in a high impedance state. Between pulses, all channels are tied to a common voltage disabled reference point.

FIG. 3 is an illustration of one embodiment of a biphasic stimulation pulse according to the teachings of the present invention. In one embodiment, the waveforms of FIG. 3 are applied to an electrical stimulation system. In another embodiment, the waveforms are applied to a pressure stimulation system. Although FIG. 3 illustrates 6 channels the discussion may be applied to a system having any number of channels and waveforms for stimulation by a movement timing stimulation systems such as system 100 of FIG. 1.

In one embodiment, an MTS system such as system 100 provides synchronized electrical stimulation through topically applied electrodes across up to 6 stimulation channels and two return channels. Over a given pulse period $Q_1$ each channel is sequentially pulsed. The pulse period $Q_1$ is the same for each channel, albeit offset in time from the other channels. In one embodiment, the pulse width $P_{w2}$ is the same for each channel. In an alternate embodiment, the pulse widths P-1 to P-6 are independently adjusted for each channel. In an alternate embodiment, the pulse widths P-1 to P-6 are independently adjusted for each channel. In this embodiment, the biphasic stimulation pulse generates a negative going pulse for a pulse width P1 and a positive going pulse after an inter pulse delay for a pulse width P2 within one pulse period Q1. In this embodiment, the inter pulse delay is 100+ microseconds. The first pulse is negative going to facilitate depolarization. The second pulse provides charge balance.

In operation, in both embodiments shown in FIG. 2 and FIG. 3, all pulse widths P1 to P-6 may be independently adjusted for each channel. A pulse width delta, Pdx, may be specified for each channel producing a resultant pulse width P1=Pw+Pd1.

In operation, in one embodiment all stimulations channels use one of two common return channels. One stimulation electrode 320-1 to 320-6 and one return electrode 320-R are active at any given time providing current flow between these electrodes. Since only one stimulation electrode 320-1 to 320-6 is active at any given time; no current flows between stimulation electrodes 320-1 to 320-6. When no stimulation pulse is active on a given channel, the channel floats in a high impedance state. Between pulses, all channels are tied to a common voltage disabled reference point.

In another embodiment, a monophasic mode may be selected whereby the pulses are the same polarity on consecutive pulses.

For all pulse types, in one embodiment, a burst count may be selected resulting in multiple pulses on a given channel for each cycle. Since the pulses for each channel are time division multiplexed, the normal time division sequence is followed until the burst count number of pulses has occurred on each channel. Approximately 100 microseconds separate the pulses on consecutive channels. The burst rate for 6 channels is computed as 1/(Sum of net channel pulse width+ 600 microseconds) for non-biphasic pulses. For biphasic pulses, an additional 100 microseconds appears between phases and the burst rate is calculated as 1/(2* Sum of net channel pulse width+1200 microseconds).

Site selection for a return electrode for a given stimulation electrode is determined by using a strategy that minimizes current flow through the torso. As an example, if three stimulation electrodes are placed on each leg, in one embodiment an individual return electrode would be placed on each leg to serve as the return for the ipsilateral stimulation electrodes. In some situations, it may be desirable to not use a common return electrode as the return current path. This may be the case when electrodes are placed around the thoracic area which could result in current flow through the torso. To avoid this situation, channels 1/2, 3/4, 5/6 and return electrode 1/return electrode 2 may be configured pair-wise such that channels 2, 4, 6 and return electrode 2 become the respective return electrodes. Variations of this configuration are also supported whereby the lower numbered channels use a common return while higher numbered channels stimulate pair-wise.

In one embodiment, gating clocks referred to as cue clocks are implemented as shown in FIG. 4. Cue clocks "A" and "B" are active during cue intervals C1. Cue clocks "Q1" through "Q4" are active for half of a cue interval. The Cue Delay D1 is the time between the active phase of cue clocks "A" and "B".

Each stimulation channel as shown in FIGS. 2 and 3 can individually be associated with a Cue clock. The stimulation pulses shown in FIG. 2 are then active only when the mapped cue clock shown in FIG. 4 is active. When channels 1/2, 3/4, and 5/6 are in pair-wise mode, the cue clock selection is disabled for channels 2, 4, and 6 as they are slaved to channels 1, 3, and 5 respectively. In one embodiment, a higher resolution of cue clocks is provided by cue clocks "V1"-"V8". Cue clocks "V1"-"V8" are active for a fourth of each "A" and "B" cue interval. The "V" clocks are thus half of a "Q" clock.

Multiple modulation schemes are applicable to improve efficacy. In one amplitude modulation scheme, the amplitude is linearly increased from 0 to the amplitude control setting over the modulation interval. In another amplitude modulation scheme, the amplitude alternates between the amplitude setting and half the amplitude setting over consecutive modulation intervals. In one embodiment, these amplitude modulation schemes reduce habituation.

Inherent in the design and application of an MTS system such as MTS 100 described with respect to FIG. 1 is the effective amplitude modulation resulting from phased activation of different electrodes. Since a given electrode will at most be enabled for a single prompt interval in each cycle, the prompt duty cycle for that electrode is less than 50% of the cue clock period. Thus, for a cue interval of 0.4 seconds and a cue delay of 0.2 seconds, a given cue will be active for 0.4 seconds and inactive for 0.8 seconds of the total 1.2 second cue clock period. This is effectively amplitude modulation.

Since MTS cueing stimulation periods are typically 12-20 milliseconds versus 5-10 milliseconds for conventional transcutaneous stimulation, MTS is less susceptible to habituation.

Frequency modulating the stimulation pulse period may also be used to reduce habituation. By linearly changing the period T1 shown in FIG. 2 over parameter selectable interval and range, the stimulation frequency changes. The range may also be randomly versus linearly changed through parameter selection.

Multi-Device Synchronization

To eliminate electrode wiring across limbs, it is desirable to have multiple MTS units with each attached to the ankle or wrist. Wiring can then be encapsulated in slip-on garments easing application for the patient or caregiver. However, in order to provide this capability, a mechanism must be provided to allow synchronization of multiple devices.

This synchronization is accomplished by producing a burst of ten, 5-10 microsecond pulses at the beginning of each stimulation pulse period indicating the beginning of a stimulation cycle. A discriminator in each MTS detects this synchronization pulse and starts the stimulation cycle. The burst is transmitted and received through the stimulation electrodes using the body as an antenna. The amplitude of these pulses is very low compared to the stimulation pulses—far below sensory threshold. Since the synchronization pulse period is very short compared to the stimulation pulse period, the synchronization burst can be easily discriminated from the stimulation pulses.

Any MTS may be the master generator for the synchronization burst. When an MTS powers up, it monitors the discriminator to detect a burst. If no burst is detected within 1 second after power up, it begins generating the burst. It then monitors for collisions and restarts the burst master detection cycle if a collision is detected.

The present invention provides systems and methods for relieving bradykinesia, akinesia and freezing in Parkinson's Disease. In one embodiment, a stimulation pulse period of 14 milliseconds is applied as shown in FIGS. 2 and 3. This is significantly higher than the 40 HZ frequency normally used for neuromuscular electrical stimulation and functional electrical stimulation and lower than the 100 HZ used for pain relief in transcutaneous electrical neural stimulators. In one embodiment, a cue clock period (2*cue interval+2*cue delay) of 1.2 seconds as shown in FIG. 4 is employed. This is significantly lower than the 5 to 20 seconds normally used for neuromuscular electrical stimulation and functional electrical stimulation. In combination the cue clock period and alternating patterns across multiple electrodes work well to relieve movement disorders.

In one embodiment a method of improving gait is provided. One embodiment of settings for and placement of electrodes is as shown in Tables 3 and 4.

TABLE 4

Electrode Placement to Improve Gait

| Channel | Location | LOC | Electrode Type | Leg |
|---|---|---|---|---|
| Return 1 | Foot | top | 8 sq. in. rectangular | right leg |
| Return 2 | Foot | top | 8 sq. in. rectangular | left leg |
| 1 | anterior tibial | above knee | 2.36 sq. in. oval | right leg |
| 2 | gastrocnemius | below knee | 2.36 sq. in. oval | right leg |
| 3 | anterior tibial | above knee | 2.36 sq. in. oval | left leg |
| 4 | gastrocnemius | below knee | 2.36 sq. in. oval | left leg |
| 5 | rectus femoris | below knee | 2.36 sq. in. oval | right leg |
| 6 | rectus femoris | below knee | 2.36 sq. in. oval | left leg |

Figure 5A:
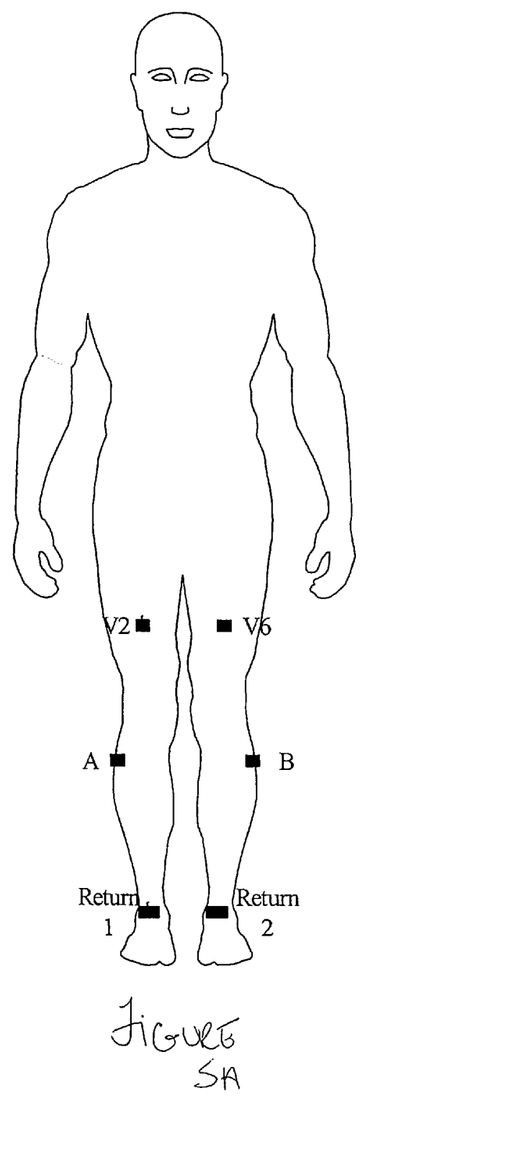
FIGS. 5a and 5b illustrate one embodiment of electrode placement for improving gait according to the teachings of the present invention.
Figure 5B:
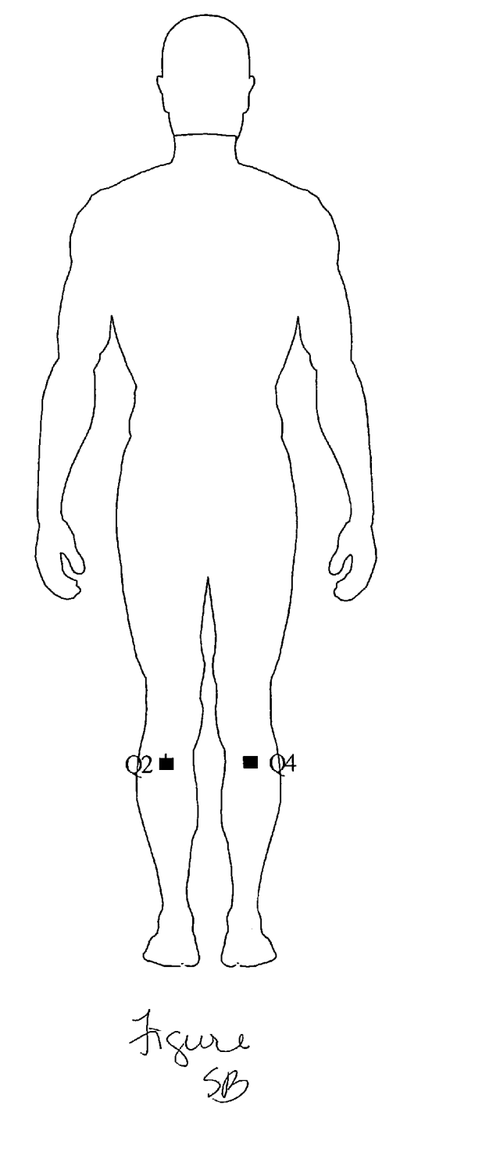

In this embodiment, electrodes are placed on both legs at stimulation points in the vicinity of motor points and this is illustrated in FIGS. 5a and 5b. In one embodiment, a pulse period of 14 milliseconds along with a pulse width of 400 microseconds is used. In other embodiments, the pulse width is adjusted to provide a comfortable level of stimulation. Channel 1 is mapped to cue clock "A" and an electrode is applied to the anterior tibial of the right leg. Channel 2 is mapped to cue clock "Q4" and an electrode is applied to the gastrocnemius on the right leg. Channel 3 is mapped to cue clock "B" and an electrode is applied to the anterior tibial of the left leg. Channel 4 is mapped to cue clock "Q2" and an electrode is applied to the gastrocnemius on the left leg. The "V2" clock interval is assigned to Channel 5 and an electrode is applied to the rectus femoris on the right leg. The "V6" clock interval is assigned to Channel 6 and an electrode is applied to the rectus femoris on the left leg.

In this embodiment, the cue interval of 0.4 seconds represents the amount of time that stimulation is applied for either the "A" or "B" clock phases configured to stimulation channels 2 and 4 respectively. The 0.2 second cue delay represents the amount of time between cue clocks "A" and "B" and between cue clocks "B" and "A". Using the following equation:

Cue clock period=2*cue interval+2*cue delay=2(0.2)+2(0.4)=1.2 seconds

The "V2" clock interval assigned to channel 5 is active for 1/4 of cue clock "A" resulting in an interval of 0.1 seconds. Channel 1 is active for the entire cue clock "A" interval of 0.4 seconds. Channels 3, 4, and 6 provide symmetrical stimulation to the left leg with cue clocks selected opposite to the right leg.

In this embodiment, stimulation electrodes each having a surface area of approximately 2.36 sq in are placed on both legs. A return electrode is placed on each foot each return electrode having a surface area of approximately 8 sq in. In one embodiment, a return electrode is placed on the top of each foot. A return electrode is active whenever a stimula-

TABLE 3

Settings to Improve Gait

| Pulse Period (milliseconds) | Pulse Width (microseconds) | Pulse Type | Cue Interval (seconds) | Cue Delay (seconds) | Cue Period/2 Channel | | | | | |
|---|---|---|---|---|---|---|---|---|---|---|
| | | | | | 1 | 2 | 3 | 4 | 5 | 6 |
| 14 | 400 | Bi-Phase | 0.4 | 0.2 | A | Q4 | B | Q2 | V2 | V6 | tion channel on the associated leg is active. This reduces current through the torso and provides a symmetrical return path.

The cue clock configuration provides sequential stimulation prompts to different muscles. The contraction of the muscle is not coincident with the stimulation prompt as would be the case with functional electrical stimulation. The cues are of insufficient amplitude to meet motor thresholds to induce contractions and are of inadequate duration to facilitate fused contractions. Unlike with functional electrical stimulation patients perform better when they do not attempt to synchronize with the cues. With the improvement of gait, patients are less fatigued. During evaluation patients have reported feeling less fatigued when using the MTS. This could be the result of Central Nervous System (CNS) controlled fused contractions of agonist muscles resulting in more uniform motion versus the choppy motion observed in PD. Uniform motion uses less energy. This is also counter to FES which results in fast fatigue of the muscles. FES facilitates contraction of fast fatigue muscle fibers first. This is contrary to the normal recruitment of slow fatigue muscle fibers first as is the case with normal CNS controlled muscle contraction.

In one embodiment a method of improving balance is provided. In one embodiment, balance is improved by using the configurations used for gait improvement as described in Tables 3 and 4 and FIG. 5 above. In one embodiment, these parameters work best for alternate action tasks such as turning in a circle.

In another embodiment, a method of improving balance for tasks requiring symmetrical contractions such as rising from a chair or reaching, the settings for and placement of electrodes is as shown in Tables 5 and 6.

TABLE 5

Settings to Improve Balance

| Pulse Period (milliseconds) | Pulse Width (microseconds) | Pulse Type | Cue Interval (seconds) | Cue Period/2 Cue Delay (seconds) | Channel 1 | 2 | 3 | 4 | 5 | 6 |
|---|---|---|---|---|---|---|---|---|---|---|
| 14 | 400 | Bi-Phase | 0.4 | 0.2 | Q3 | Q4 | Q3 | Q4 | Q2 | Q2 |

TABLE 6

Electrode Placement to Improve Balance

| Channel | Location | LOC | Electrode Type | Leg |
|---|---|---|---|---|
| Return 1 | Foot | Top | 8 sq. in. rectangular | Right leg |
| Return 2 | Foot | Top | 8 sq. in. rectangular | left leg |
| 1 | anterior tibial | above knee | 2.36 sq. in. oval | Right leg |
| 2 | gastrocnemius | below knee | 2.36 sq. in. oval | Right leg |
| 3 | anterior tibial | above knee | 2.36 sq. in. oval | left leg |
| 4 | gastrocnemius | below knee | 2.36 sq. in. oval | left leg |
| 5 | rectus femoris | below knee | 2.36 sq. in. oval | Right leg |
| 6 | rectus femoris | below knee | 2.36 sq. in. oval | left leg |

In one embodiment a method of relieving arm bradykinesia is provided. Arm swing impairments are common in Parkinson's Disease and electrode placement strategies are focused on anticipated arm swing improvements. In one embodiment, electrode placement prompts flex at the elbow and arm swing at the shoulder. One embodiment of settings for and placement of electrodes is as shown in Tables 7 and 8.

TABLE 7

Settings to Improve Arm Swing

| Pulse Period (milliseconds) | Pulse Width (microseconds) | Pulse Type | Cue Interval (seconds) | Cue Period/2 Cue Delay (seconds) | Channel 1 | 2 | 3 | 4 | 5 | 6 |
|---|---|---|---|---|---|---|---|---|---|---|
| 14 | 200 | Alternating Phase | 0.4 | 0.2 | B | A | B | A | | |

TABLE 8

Electrode Placement to Improve Arm Swing

| Channel | Location | LOC | Electrode Type |
|---|---|---|---|
| Return 1 | Trapezius | Back | 8.0 sq. in. rectangular |
| 1 | Triceps | above elbow | 2.36 sq. in. oval |
| 2 | brachioradialis | below elbow | 2.36 sq. in. oval |

TABLE 8-continued

Electrode Placement to Improve Arm Swing

| Channel | Location | LOC | Electrode Type |
|---|---|---|---|
| 3 | Anterior deltoid | Shoulder (back) | 2.36 sq. in. oval |
| 4 | Posterior deltoid | Shoulder (front) | 2.36 sq. in. oval |

Figure 6:
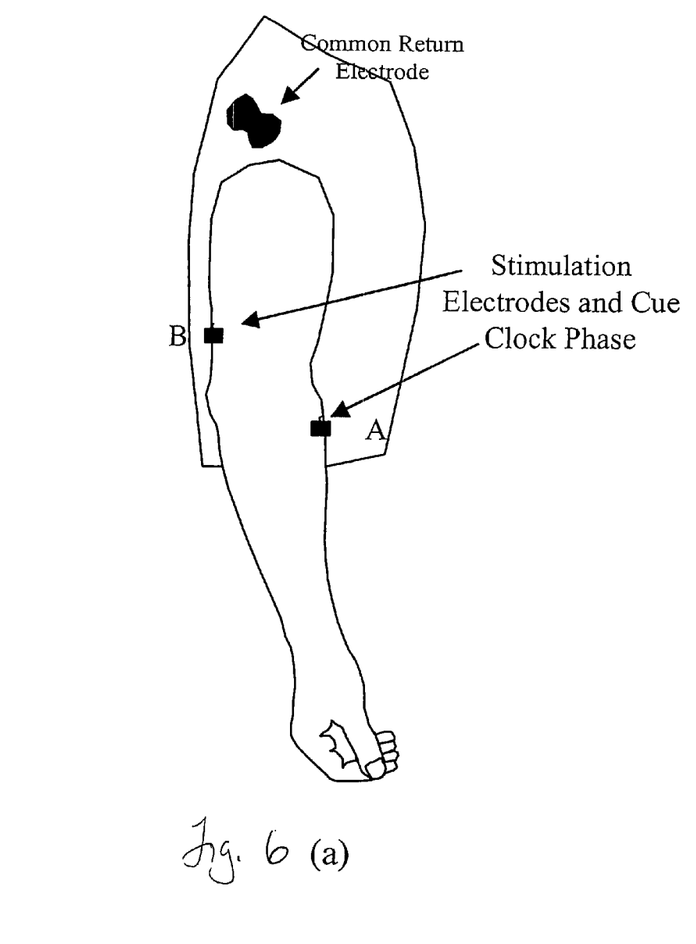
FIGS. 6a and 6b illustrate two embodiments of electrode placement for relieving arm bradykinesia according to the teachings of the present invention.

FIG. 6(a) illustrates one embodiment of electrode placement for relieving arm bradykinesia having two electrodes A and B to prompt elbow flexion and extension. The arm swing is not synchronized with the stimulation prompts. In one embodiment, electrodes are placed on the arm at stimulation points in the vicinity of motor points and this is illustrated in FIG. 6(a).

FIG. 6(b) illustrates an embodiment of electrode placement for relieving arm bradykinesia having four electrodes to prompt elbow flexion and extension and arm swing at the shoulder. One electrode is associated with cue clock "B" and is applied to the triceps prompts extension of the elbow to swing the arm back. Another electrode is associated with cue clock "A" and is applied to the brachioradialis and prompts flex of the elbow to facilitate swing of the arm forward. Two electrodes one associated with cue clock A and another associated with cue clock B are applied to the anterior and posterior deltoids, respectively, and prompt shoulder movement. In one embodiment, electrodes are placed on an arm at stimulation points in the vicinity of motor points and this is illustrated in FIG. 6(b).

Although the placement strategies have been described with respect to arm swing, these same movements are required for reaching, pointing, and elbow flex required for eating. The above described electrode placements will facilitate generic arm movements.

In one embodiment, a common return electrode is utilized for both the left and right arms. In one embodiment, the common return electrode is placed on top of the shoulder. By placing the common return electrode on top of the shoulder, current flow through the torso is minimized.

In one embodiment a method of improving arm movement and handwriting is provided. Arm movement impairments are common in Parkinson's Disease. These movements may be associated with drawing, handwriting or activities of daily living, such as, eating. One embodiment of settings for and placement of electrodes for improving arm movement is as shown in Tables 9 and 10. In this embodiment, electrode placement is focused on improving these arm movements. As discussed previously, in one embodiment, the arm movement is not synchronized with the prompts as would be the case with functional electrical stimulation.

TABLE 9

Settings to Improve Arm Movement

| Pulse Period (milliseconds) | Pulse Width (microseconds) | Pulse Type | Cue Interval (seconds) | Cue Period/2 Cue Delay (seconds) | Channel 1 | 2 | 3 | 4 | 5 | 6 |
|---|---|---|---|---|---|---|---|---|---|---|
| 14 | 200 | Alternating Phase | 0.1 | 0.5 | Q3 | Q1 | Q1 | Q3 | Q1 | Q1 |

TABLE 10

Electrode Placement to Improve Arm Movement

| Channel | Location | LOC | Electrode Type |
|---|---|---|---|
| Return 1 | Trapezius | back | 8.0 sq. in. |
| 1 | Interossei | Top of hand | 2.36 sq. in. oval |
| 2 | flexor digitorum | Near motor point | 2.36 sq. in. oval |
| 3 | ulnar flexor | Near motor point | 2.36 sq. in. oval |
| 4 | Brachioradialis | Near motor point | 2.36 sq. in. oval |
| 5 | Triceps | Above elbow | 2.36 sq. in. oval |
| 6 | deltoid - medial | Near motor point | 2.36 sq. in. oval |

Figure 7:
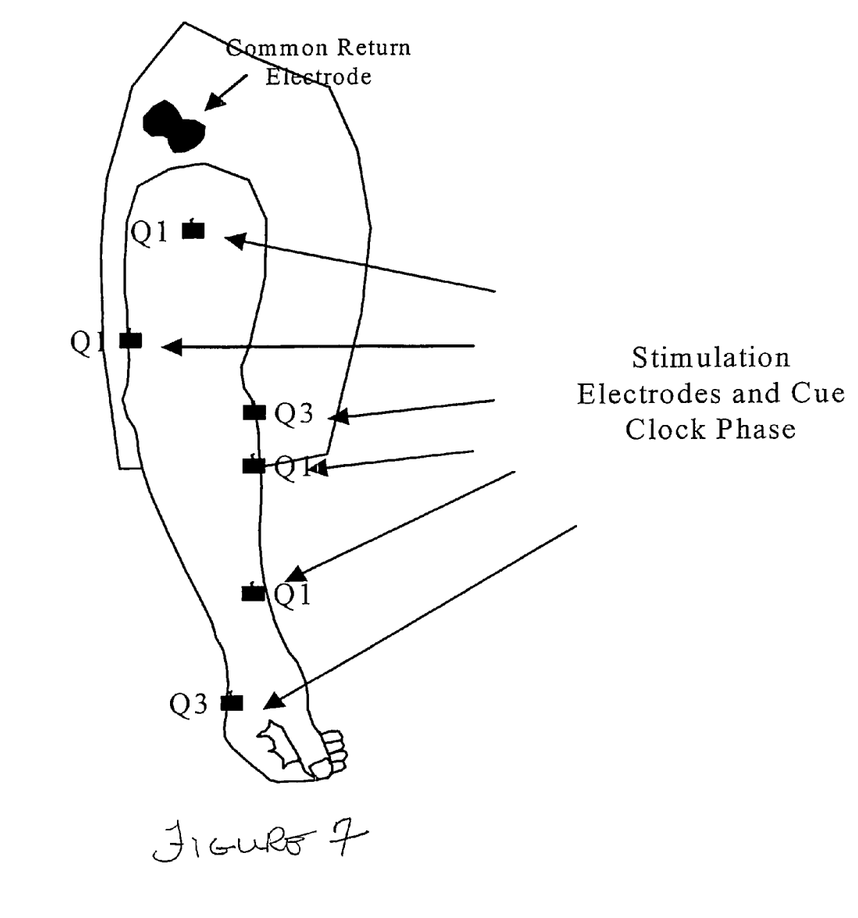
FIG. 7 illustrates one embodiment of electrode placement for improving arm movement according to the teachings of the present invention.

FIG. 7 illustrates one embodiment of electrode placement for improving arm movements having six electrodes 4-Q1s and 2-Q3s to prompt arm movement such as drawing, handwriting, or other activities of daily living. The arm movement is not synchronized with the stimulation prompts. In one embodiment, electrodes are placed on an arm at stimulation points in the vicinity of motor points and this is illustrated in FIG. 7.

In one embodiment, a method of electrode placement to reduce tremor is provided. One embodiment of settings for and placement of electrodes to reduce tremor is as shown in Tables 11 and 12. The method does not rely on forcing muscle contraction. As with the bradykinesia method, the stimulation prompts are not synchronized with movement or the tremor. In this embodiment, intensity settings are adjusted below motor threshold. One embodiment, of parameter settings are as shown in Table 11. The cue selected is shown as "On". This indicates that the cue is active (On) whenever cue clock 'A' or 'B' is active. This produces an effective cue clock frequency of 1.67 hertz. The frequency is below the 4-6 hertz rest tremor associated with Parkinson's Disease.

For clarity in location of electrodes, multiple channels are used to enable the stimulation electrodes as shown in Table 12. Since all stimulation electrodes are slaved to the same cue clocks, a virtual single stimulation electrode is realized that encircles the forearm below the elbow. In one embodiment, electrodes are placed on the arm at stimulation points in the vicinity of motor points.

TABLE 11

Settings to Reduce Tremor

| Pulse Period (milliseconds) | Pulse Width (microseconds) | Pulse Type | Cue Period/2 | | Channel | | | | | |
| --- | --- | --- | --- | --- | --- | --- | --- | --- | --- | --- |
| | | | Cue Interval (seconds) | Cue Delay (seconds) | 1 | 2 | 3 | 4 | 5 | 6 |
| 14 | 200 | Bi-Phase | 0.1 | 0.5 | On | On | On | On | On | |

TABLE 12

Electrode Placement to Reduce Tremor

| Channel | Location | LOC | Electrode Type |
| --- | --- | --- | --- |
| Return 1 | Trapezius | Back | 8.0 sq. in. rectangular |
| 1 | Brachioradialis | Near motor point | 2.36 sq. in. oval |
| 2 | Pronator teres | Near motor point | 2.36 sq. in. oval |
| 3 | Radialis brevis | Near motor point | 2.36 sq. in. oval |
| 4 | Radialis longus | Near motor point | 2.36 sq. in. oval |
| 5 | Extensor ulnaris | Near motor point | 2.36 sq. in. oval |

Embodiments of the present invention provide adjunctive therapy to medication for movement disorders, relieve bradykinesia, symptomatic relief through on/off fluctuations, relieve start hesitation and freezing and the like. Embodiments of the present invention further helps patients focus on tasks for gait training in physical, facilitates exercise and the like.

Embodiments of the present invention are not limited to cutaneous electrical stimulation, once application points for efficacy are identified stimulators planted under the skin to stimulate afferents are also employable. In one embodiment, the stimulators are controlled by a wireless link adjusting parameters and synchronizing stimulation. In contrast to deep brain stimulation stimulators planted under the skin to stimulate afferents would not be as invasive. The risks associated with brain surgery of cranial infection, hemorrhage or blindness could thus be avoided.

In one embodiment, for electrical stimulation, it is anticipated that electrodes applied near motor points will provide the most effective placements. Stimulation levels will be most effective for relief of PD symptoms when stimulation facilitates central nervous system induced contraction of muscles associated with one or more stimulation points.

Stimulation patterns and waveforms may be statically selected based on the task, such as, walking, writing, or pointing. Waveforms could also be modified based on input from external sensors. These sensors could be placed on the body to measure accelerations, orientation of different body parts relative to a gravity vector, and pressures associated with tactile and topical feedback.

CONCLUSION

Embodiments of the present invention have been described. The embodiments provide movement-timing stimulators that aid in the relief of the symptoms of neurological movement disorders by providing sensing and stimulation at various locations of the body of a living subject.

Although specific embodiments have been illustrated and described in this specification, it will be appreciated by those of ordinary skill in the art that any arrangement that is calculated to achieve the same purpose may be substituted for the specific embodiment shown. This application is intended to cover any adaptations or variations of the present invention. For example, although this technology is primarily being developed to relieve symptoms of neurological movement disorders, it has potential for application in other areas. These include symptomatic relief for other disorders, such as, Huntington's disease and rehabilitation therapy for neurological damage. Other applications may include incorporation into flight suits to prevent spatial disorientation of aircrew undergoing high acceleration maneuvers and potential for relieving symptoms of motion sickness.

What is claimed is:

1. A method of improving a patient's gait, the method comprising:
    producing a plurality of stimulation prompts at a plurality of stimulation points using multiple stimulation channels;
    wherein the plurality of stimulation points are located symmetrically on each leg;
    applying the plurality of stimulation prompts in a timed periodic fashion across the plurality of stimulation points;
    wherein the plurality of stimulation prompts are not synchronized with the patient's gait and do not force muscle contraction;
    wherein each of the multiple stimulation channels is associated with a stimulation electrode at one of the plurality of stimulation points; and
    activating a return electrode whenever one of the multiple stimulation channels on an associated leg is active.

2. The method of claim 1, wherein the plurality of stimulation prompts each have a stimulation pulse period of approximately 14 milliseconds.

3. The method of claim 1, wherein the plurality of stimulation points are associated with a plurality of muscles and contraction of the plurality of muscles is not coincident with the corresponding stimulation prompt.

4. The method of claim 1, further comprising setting the intensity of the plurality of stimulation prompts below motor threshold for muscles associated with the plurality of stimulation points.

5. The method of claim 1, further comprising setting the amplitude of the plurality of stimulation prompts below motor thresholds to facilitate central nervous system induced contractions of muscles associated with the plurality of stimulation points.

6. The method of claim 1, further comprising setting the duration of the plurality of stimulation prompts to facilitate central nervous system induced fused contractions of muscles associated with the plurality of stimulation points.

7. The method of claim 1, wherein producing a plurality of stimulation prompts at a plurality of stimulation points using multiple stimulation channels comprises producing stimulation prompts in the vicinity of motor points of the anterior tibial muscle, gastrocnemius muscle, and rectus femoris muscle on each leg.

8. The method of claim 1, wherein producing a plurality of stimulation prompts comprises sequentially producing stimulation prompts at stimulation points near the anterior tibial muscle on the right leg, the gastrocnemius muscle on the right leg, the anterior tibial muscle on the left leg, the gastrocnemius muscle of the left leg, the rectus femoris muscle of the right leg and the rectus femoris muscle of the left leg.

9. The method of claim 1, wherein each stimulation channel is individually associated with a cue clock.

10. The method of claim 9, wherein a first channel is associated with a first cue clock and stimulation pulses for an associated stimulation electrode are active when the first cue clock is active.

11. The method of claim 10, wherein the first cue clock is active during a first cue interval.

12. The method of claim 10, wherein a second channel is associated with a second cue clock and stimulation pulses for an associated stimulation electrode are active when the second cue clock is active.

13. The method of claim 12, wherein the second cue clock is active during a second half of a second cue interval.

14. The method of claim 11, wherein the first cue interval is approximately 0.4 seconds.

15. The method of claim 13, wherein the second cue interval is approximately 0.4 seconds.

16. The method of claim 12, wherein a third channel is associated with a third cue clock and stimulation pulses for an associated stimulation electrode are active when the third cue clock is active.

17. The method of claim 16, wherein the third cue clock is active during a second quarter of the first cue interval.

18. The method of claim 16, wherein the first, second and third cue clocks are associated with stimulation electrodes located on one leg.

19. The method of claim 18, wherein fourth, fifth and sixth channels are associated with fourth, fifth and sixth cue clocks, wherein the fourth, fifth and sixth cue clocks are active during the same portion of opposite cue intervals to the first, second and third cue clocks.

20. The method of claim 2, wherein the stimulation pulse has a pulse width of approximately 400 microseconds.

21. The method of claim 1, further comprising applying stimulation pulses for each of the multiple stimulation channels in a bi-phasic manner.

22. The method of claim 1, further comprising time division multiplexing stimulation pulses for each of the multiple stimulation channels.

23. The method of claim 1, wherein stimulation current for the stimulation prompts is approximately 10 milliamps.

24. A method of reducing habituation in improving a patient's gait, the method comprising:
producing a plurality of stimulation prompts at a plurality of stimulation points using multiple stimulation channels;
wherein the plurality of stimulation points are located symmetrically on each leg;
applying the plurality of stimulation prompts in a timed periodic fashion across the plurality of stimulation points;
wherein the plurality of stimulation prompts are not synchronized with the patient's gait and do not force muscle contraction;
wherein each of the multiple stimulation channels is associated with a stimulation electrode at one of the plurality of stimulation points; and
activating a return electrode whenever one of the multiple stimulation channels on an associated leg is active;
linearly changing a pulse period for the plurality of stimulation prompts.

* * * * *